United States Patent
Walsh

(10) Patent No.: US 8,816,684 B2
(45) Date of Patent: Aug. 26, 2014

(54) NOISE CANCELING IN-SITU NMR DETECTION

(75) Inventor: David O. Walsh, Mukilteo, WA (US)

(73) Assignee: Vista Clara Inc., Mukilteo, WA (US)

( * ) Notice: Subject to any disclaimer, the term of this patent is extended or adjusted under 35 U.S.C. 154(b) by 903 days.

(21) Appl. No.: 12/914,138

(22) Filed: Oct. 28, 2010

(65) Prior Publication Data

US 2011/0109311 A1 May 12, 2011

Related U.S. Application Data

(60) Provisional application No. 61/259,280, filed on Nov. 9, 2009.

(51) Int. Cl.

| | | |
|---|---|---|
| *G01V 3/10* | (2006.01) | |
| *G01V 3/14* | (2006.01) | |
| *G01V 3/18* | (2006.01) | |
| *G01V 3/28* | (2006.01) | |
| *G01V 3/32* | (2006.01) | |
| G01V 3/36 | (2006.01) | |
| G01N 24/08 | (2006.01) | |
| G01R 33/36 | (2006.01) | |

(52) U.S. Cl.
CPC .. *G01V 3/32* (2013.01); *G01V 3/28* (2013.01); *G01V 3/18* (2013.01); *G01V 3/14* (2013.01); *G01V 3/10* (2013.01); *G01V 3/36* (2013.01); *G01N 24/081* (2013.01); *G01R 33/36* (2013.01)
USPC ............ 324/303; 324/307; 324/318; 324/320

(58) Field of Classification Search
USPC .................. 324/300–322, 254; 600/407–435; 382/128–131
See application file for complete search history.

(56) References Cited

U.S. PATENT DOCUMENTS

| | | | | |
|---|---|---|---|---|
| 2,973,471 | A | * | 2/1961 | Armistead et al. ............ 324/303 |
| 3,019,383 | A | | 1/1962 | Varian |
| 3,159,785 | A | * | 12/1964 | Beynon ......................... 324/254 |
| 4,727,324 | A | | 2/1988 | Bendall et al. |
| 4,812,760 | A | | 3/1989 | Bottomley |
| 4,975,644 | A | | 12/1990 | Fox |
| 5,144,243 | A | | 9/1992 | Nakabayashi |
| 5,545,995 | A | | 8/1996 | Schneider et al. |
| 5,578,920 | A | * | 11/1996 | Kuster et al. ................... 324/301 |

(Continued)

FOREIGN PATENT DOCUMENTS

| | | |
|---|---|---|
| EP | 0170508 | 9/1990 |
| EP | 04777777 | 5/2006 |

(Continued)

OTHER PUBLICATIONS

Hayes et al.: "Volume Imaging with MR Phased Arrays"; Magn. Res. Med. 18, 309-319 (1991).
Katscher et al.: "Transmit SENSE"; Mag. Res. Med. 49, 144-156 (2003).

(Continued)

*Primary Examiner* — Melissa Koval
*Assistant Examiner* — Tiffany Fetzner
(74) *Attorney, Agent, or Firm* — Jensen & Puntigam, PS

(57) ABSTRACT

Technologies applicable to noise canceling in-situ NMR detection and imaging are disclosed. An example noise canceling in-situ NMR detection apparatus may comprise one or more of a static magnetic field generator, an alternating magnetic field generator, an in-situ NMR detection device, an auxiliary noise detection device, and a computer.

35 Claims, 10 Drawing Sheets

(56) References Cited

U.S. PATENT DOCUMENTS

| | | | |
|---|---|---|---|
| 5,759,152 | A | 6/1998 | Felmlee |
| 5,796,252 | A * | 8/1998 | Kleinberg et al. ............ 324/303 |
| 6,107,797 | A | 8/2000 | Sezginer |
| 6,160,398 | A | 12/2000 | Walsh |
| 6,201,395 | B1 | 3/2001 | Stanley |
| 6,366,086 | B1 | 4/2002 | Sen |
| 6,477,398 | B1 | 11/2002 | Mills |
| 6,593,740 | B1 | 7/2003 | Van Den Brink et al. |
| 6,845,262 | B2 | 1/2005 | Albert |
| 6,924,644 | B2 * | 8/2005 | Suits et al. .................... 324/318 |
| 6,969,992 | B2 | 11/2005 | Vaughan |
| 7,035,682 | B2 | 4/2006 | Van Den Brink et al. |
| 7,176,689 | B2 | 2/2007 | Machida |
| 7,221,160 | B2 | 5/2007 | Leussler |
| 7,414,402 | B2 | 8/2008 | Habera |
| 7,466,128 | B2 | 12/2008 | Walsh |
| 7,771,341 | B2 * | 8/2010 | Rogers .............................. 600/9 |
| 7,884,609 | B2 * | 2/2011 | Soutome et al. ............. 324/322 |
| 2003/0122545 | A1 | 7/2003 | Van Den Brink et al. |
| 2004/0066194 | A1 * | 4/2004 | Slade et al. .................... 324/318 |
| 2005/0057251 | A1 * | 3/2005 | Suits et al. .................... 324/309 |
| 2006/0186882 | A1 | 8/2006 | Walsh |
| 2009/0021256 | A1 * | 1/2009 | Soutome et al. .............. 324/318 |
| 2011/0095758 | A1 | 4/2011 | Walsh |
| 2011/0109311 | A1 * | 5/2011 | Walsh .......................... 324/309 |

FOREIGN PATENT DOCUMENTS

| | | |
|---|---|---|
| EP | 1651974 | 4/2011 |
| GB | 2339024 | 12/2000 |
| WO | 2004061469 | 7/2004 |
| WO | 2005017549 | 2/2005 |
| WO | 2007030832 | 3/2007 |

OTHER PUBLICATIONS

Legchenko, "A Revised Mathematical Model of Magnetic Resonance Sounding", presented at the MRS_2nd International Workshop, Nov. 19-21, 2003 in Orleans, France.

Hertrich, "Surface-NMR with Separated Loops-Investigations on Spatial Resolution", presented at the MRS_2nd International Workshop, Nov. 19-21, 2003 in Orleans France.

Warsa et al., "3-D Modelling and Assessment of 2-D inversion of Surface NMR", presented at the MRS-2nd International Workshop, Nov. 19-21, 2003 in Orleans, France.

Legchenko, "Industrial Noise and Processing of the Magnetic Resonance Signal", presented at the MRS_2nd International Workshop, Nov. 19-21, 2003 in Orleans, France.

Walsh, "Adaptive Reconstruction of Phased Array MR Imagery", Magn. Res. Med. 43, 582-590 (2000).

Ryu, Si Ung, International Search Report for PCT/US08/082969, Apr. 10, 2009, 3 pages.

Walsh, filing receipt for U.S. Appl. No. 12/715,115 (reissue of 7,466,128, cited above), filed Mar. 1, 2010.

Giovannetti, Note: Magnetostatic Simulation for Accurate Design of Low-Field MRI Phased Array Coils, 7 pages, Feb. 27, 2007.

Krjukov, "Design and Evaluation of a Low Field System for Hyperpolarized 3-He Gas Imaging of Neonatal Lungs" 4 pages, Jun. 22, 2007.

Leussler, "Intrinsic Hybrid Surface Coil Array for Improved SNR in Cardiac MRI", 2 pages, (2002), pp. 24-25.

De Zanche, "Principles of Array System Design", 8 pages, (2006) cited from ISMRM Seatle.

Zwart, "Design of a SENSE-Optimized High-Sensitivity MRI Receive Coil for Brain Imaging", 10 pages, Jan. 31, 2002.

Lersch, Communication in EU Application No. 08848565.1, Including Supplementary EU Search Report, Dated Dec. 30, 2010, 19 pages.

* cited by examiner

NOISE CANCELING IN-SITU NMR DETECTION

STATEMENT OF GOVERNMENT SUPPORT

This invention was made with Government support under Agreement No. DE FG02-07ER84931 awarded by the Department of Energy. The Government has certain rights in this invention.

CROSS REFERENCE TO RELATED APPLICATIONS

Priority is claimed to U.S. Provisional Patent Application No. 61/259,280, filed on Nov. 9, 2009, entitled "IN-SITU NMR DETECTION APPARATUS WITH NOISE CANCELLING ANTENNAS," the disclosure of which is incorporated herein by reference in its entirety.

BACKGROUND

Nuclear Magnetic Resonance (NMR) systems have been in use for many years and can be used to provide imaging and/or analysis of a sample being tested. For example, U.S. Pat. No. 7,466,128, U.S. Pat. No. 6,160,398, and PCT/US2008/082969 describe a variety of NMR technologies, and are incorporated herein by reference. Various different types of NMR are known, including laboratory NMR spectroscopy that places the sample under investigation inside a detection coil, and in-situ or "inside out" NMR that places a detection coil inside or adjacent to a sample under investigation. Existing in-situ NMR devices have deficiencies in their ability to cancel Radio Frequency (RF) or other Electromagnetic (EM) noise in the vicinity of the in-situ NMR measurement.

SUMMARY

Technologies applicable to noise canceling in-situ NMR detection and imaging are disclosed. An example noise canceling in-situ NMR detection apparatus may comprise one or more of a static magnetic field generator, an alternating magnetic field generator, an in-situ NMR detection device, an auxiliary noise detection device, and a computer. The computer may optionally be configured to control the various other components. The NMR detection device may comprise a noise canceling design in some embodiments. In some embodiments, the computer may be configured to subtract noise measurement information from NMR measurement information, to produce output in-situ NMR measurement data with attenuated noise. Further aspects and variations are discussed in detail below.

BRIEF DESCRIPTION OF THE DRAWINGS

Various features and attendant advantages of the disclosed technologies will become fully appreciated when considered in conjunction with the accompanying drawings, in which like reference characters designate the same or similar parts throughout the several views, and wherein.

DETAILED DESCRIPTION

Figure 1:
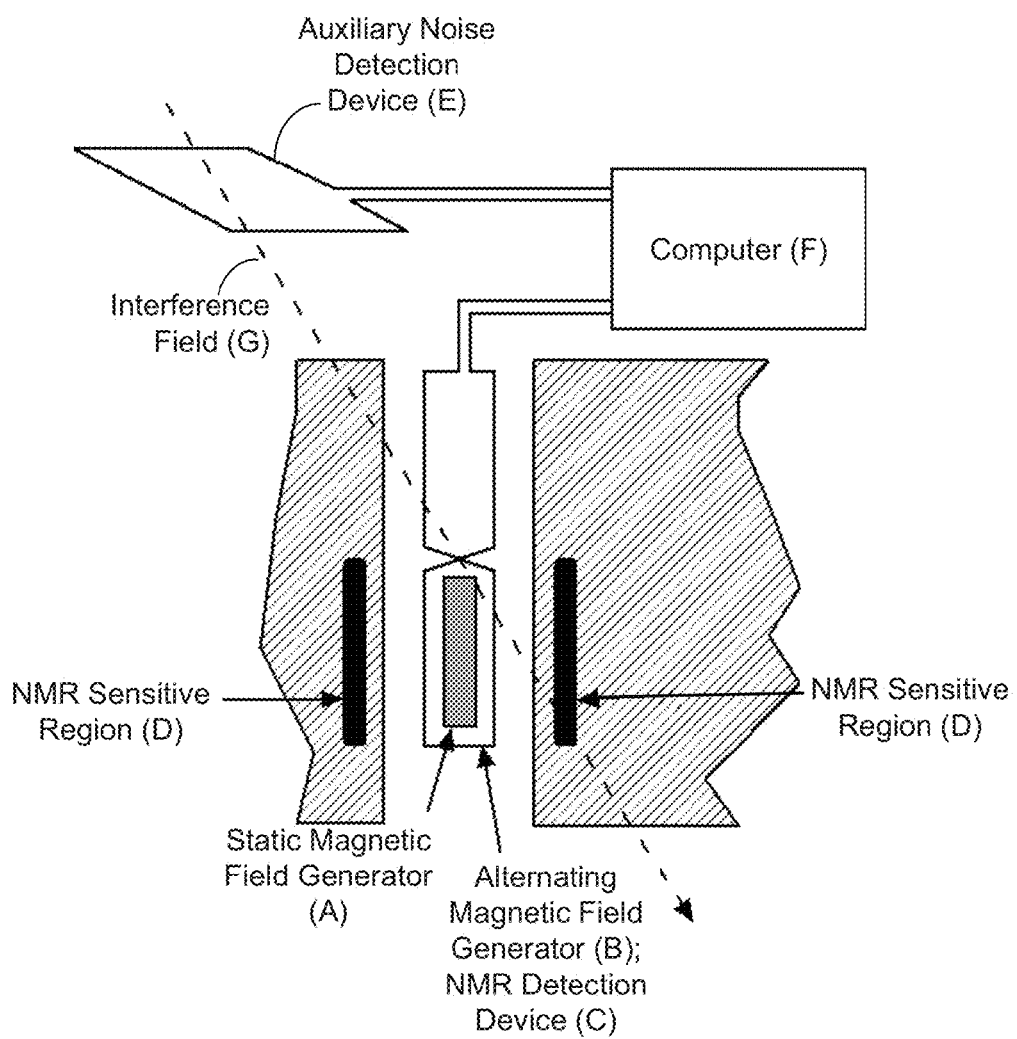
FIG. 1 is a diagram illustrating example components of noise canceling in-situ NMR detection apparatus in accordance with some embodiments of the present disclosure.

Prior to explaining at least one embodiment of the invention in detail, it is to be understood that the invention is not limited to the details of construction or arrangements of the components and method steps set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

Overview

Technologies for noise canceling in-situ NMR may include, inter alia, components and methods configured to generate a static magnetic field B0 within a sample of interest, components and methods configured to generate an alternating magnetic field B1 to actuate an NMR process within the sample of interest, components and methods configured to detect the actuated NMR process from within the sample of interest, and/or components and methods configured to attenuate noise.

Applications of noise canceling in-situ NMR may include, inter alia, the use of NMR detection devices inside boreholes to detect and characterize the NMR properties of fluids in Earth formations, the use of NMR detection devices in bulk samples to characterize the NMR properties of said samples, and the use of NMR detection devices inserted into human patients to determine the NMR properties of fluids or tissues. The technologies disclosed herein are generally discussed in the context of borehole NMR, but it will be appreciated that the disclosed technologies may be adapted to any application of in-situ NMR.

FIG. 1 is a diagram illustrating example components of noise canceling in-situ NMR detection apparatus in accordance with some embodiments of the present disclosure. With reference to FIG. 1, components and methods configured to generate a static magnetic field B0 within a sample of interest may comprise a static magnetic field generator (A) and the use thereof. Components and methods configured to generate an alternating magnetic field B1 to actuate an NMR process within the sample of interest may comprise an alternating magnetic field generator (B) and the use thereof, noting that the alternating magnetic field generator (B) is shown descriptively in this embodiment as an induction coil, which may be used to generate an alternating magnetic field in an NMR sensitive region (D) within a sample of interest. Components and methods configured to detect the actuated NMR process within the sample of interest may comprise a NMR detection device (C) and the use thereof. NMR detection device (C) is shown as an induction coil, which may be configured to detect NMR in an NMR sensitive region (D) from within a sample of interest, and noting that in the illustrated embodiment the same induction coil is used to generate the alternating magnetic field and to detect the resulting NMR signal process. In some embodiments, components and methods configured to attenuate noise may comprise the NMR detection device (C), when configured to attenuate noise as described herein. In some embodiments, components and methods configured to attenuate noise may comprise an auxiliary noise detection device (E) that may be configured detect an electromagnetic noise or interference field (G). Embodiments using an auxiliary noise detection device (E) may be used in combination with an NMR detection device (C) that is configured to attenuate noise in some embodiments, or may be used in combination with an NMR detection device (C) that is not configured to attenuate noise.

In some embodiments, any and all of the various components and methods illustrated in FIG. 1 may be configured to operate under control of or in communication with computer (F). Computer (F) may be configured to control the NMR measurement sequence, e.g., as discussed in connection with FIG. 2. Computer (F) may include an NMR spectrometer configured to sample and record signals from the NMR detection device (C) and/or the auxiliary noise detection device (E). Computer (F) may comprise a power amplifier configured to drive the alternating magnetic field generator (B) and/or static magnetic field generator (A). Computer (F) may comprise transmit and receive switches configured to activate the alternating magnetic field generator (B) in transmit mode, and to activate the NMR detection device (C) in receive mode. Computer (F) may comprise matching circuits and receive electronics. Said matching circuits may be designed to optimize the transmission of the NMR activating signals and/or the detected NMR signals. The receive electronics may include preamplifiers, switching circuits, filters, buffer amplifiers, and other preconditioning circuitry. Computer (F) may comprise a data acquisition system configured to receive, process and record NMR measurement information and/or noise measurement information.

Figure 2:
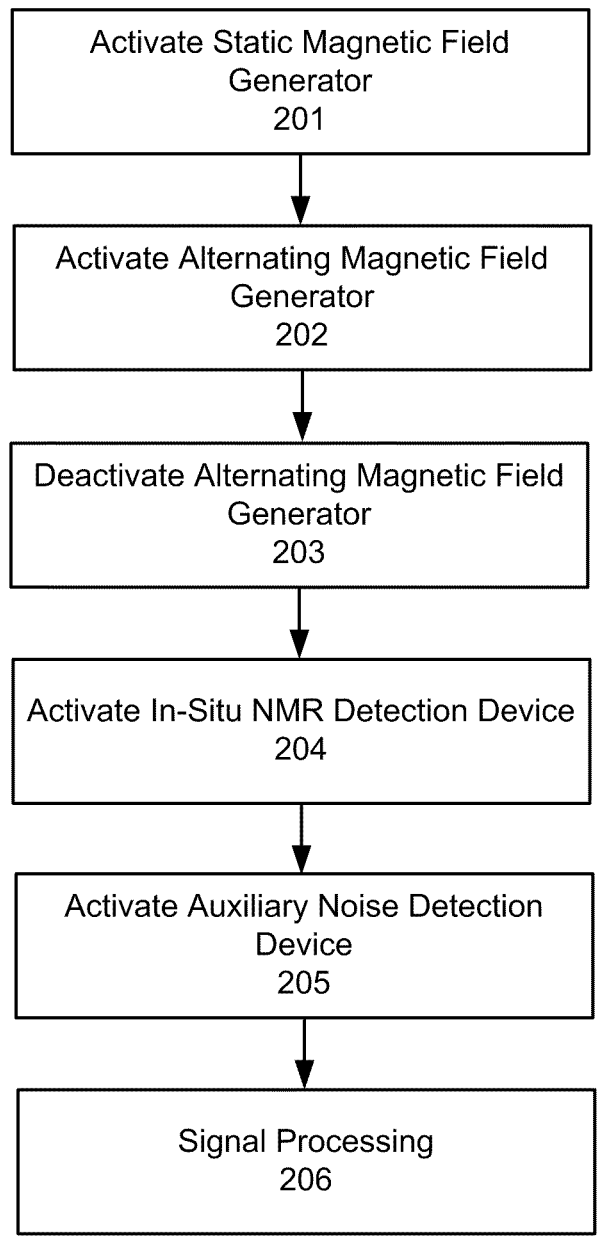
FIG. 2 is a diagram illustrating an example method as may be performed in connection with the various systems disclosed herein.
Figure 9:
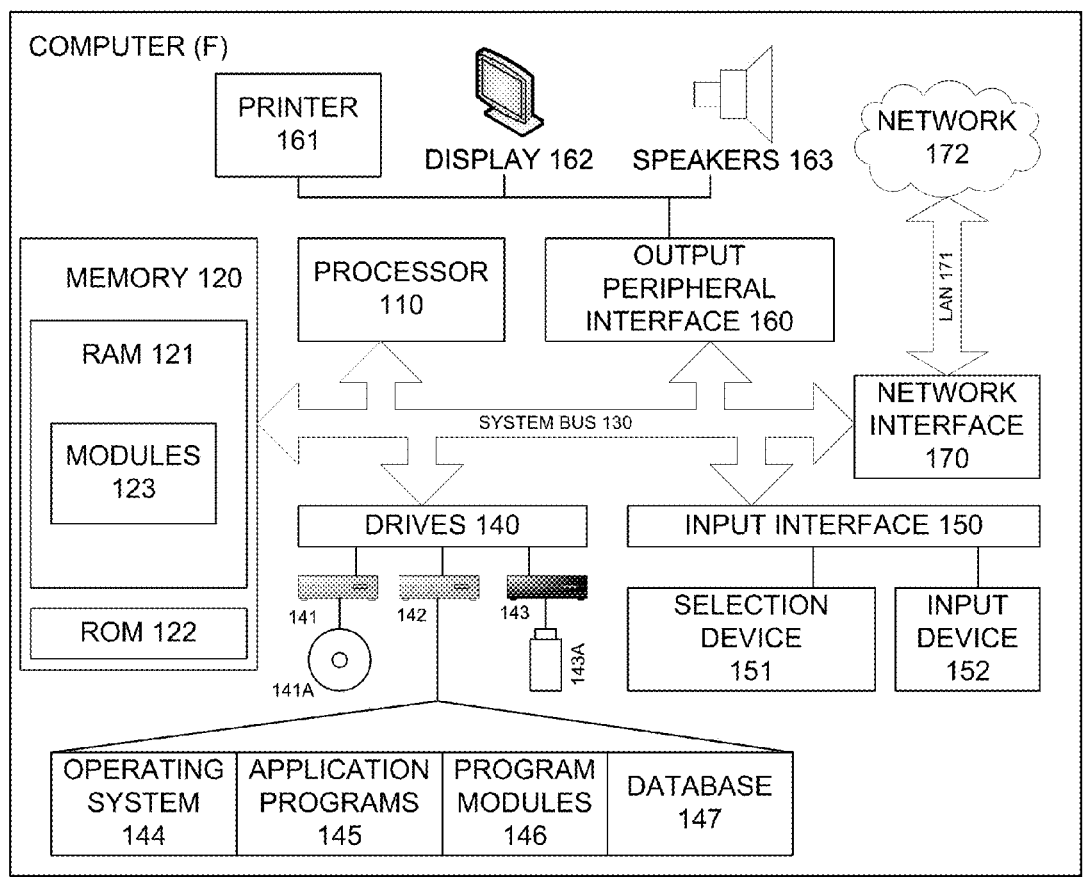
FIG. 9 is a diagram illustrating an example computing device as may be configured to perform aspects of this disclosure.

FIG. 2 is a diagram illustrating an example method as may be performed in connection with the various systems disclosed herein. FIG. 2 may also be viewed as representing operations executable by a computer, e.g., as illustrated in FIG. 9, and corresponding modules or instructions stored on a computer readable medium. FIG. 2 includes a "Activate Static Magnetic Field Generator" operation 201, a "Activate Alternating Magnetic Field Generator" operation 202, a "Deactivate Alternating Magnetic Field Generator" operation 203, a "Activate In-Situ NMR Detection Device" operation 204, a "Activate Auxiliary Noise Detection Device" operation 205, and a "Signal Processing" operation 206.

In a "Activate Static Magnetic Field Generator" operation 201, the computer (F) may be configured to position a static magnetic field generator near a sample of interest. The static magnetic field generator may also be positioned manually or using electronics not controlled by the computer (F). In embodiments in which the static magnetic field generator comprises an electromagnet or other device that can be turned on and off, the magnet may be activated or otherwise adjusted to produce a desired static magnetic field in a sample of interest.

In a "Activate Alternating Magnetic Field Generator" operation 202, the computer (F) may be configured to route electrical current to a alternating magnetic field generator such as (B), for example by activating a power amplifier and closing a transmit switch which allows current to flow from the power amplifier to the alternating magnetic field generator (B). When the alternating magnetic field generator is activated, the system may be described as in transmit mode.

In a "Deactivate Alternating Magnetic Field Generator" operation 203, the computer (F) may be configured to shut off electrical current from an alternating magnetic field generator (B), for example by deactivating the power amplifier and/or opening the transmit switch and otherwise controlling appropriate switches or other electronics. Operation 203 may result in the system exiting transmit mode.

In a "Activate In-Situ NMR Detection Device" operation 204, the computer (F) may be configured to activate appropriate switches or other electronics to "listen" to signals from an in-situ NMR detection device such as (C). For example a receive mode switch may be closed to connect NMR detection device (C) with primary detection channel electronics. Incoming signals from the in-situ NMR detection device may be modified and sampled and otherwise processed as described herein. When the in-situ NMR detection device is activated, the system may be described as in receive mode.

In a "Activate Auxiliary Noise Detection Device" operation 205, the computer (F) may be configured to activate appropriate switches or other electronics to "listen" to signals from an auxiliary noise detection device such as (E). For example, noise signal receive switches may be closed to connect auxiliary noise detection device (E) with auxiliary detection channel electronics. Incoming signals from the auxiliary noise detection device may be modified and sampled and otherwise processed as described herein. Operation 205 does not necessarily occur after operation 204, the two operations may overlap or happen concurrently in some embodiments.

In a "Signal Processing" operation 206, the computer (F) may be configured to process signals from the in-situ NMR detection device and/or auxiliary noise detection device to produce an output. Signal processing is discussed further with reference to FIGS. 7-10.

It should be noted that in some embodiments of FIG. 2, one or more of the illustrated operations may not be necessary, while in some embodiments, additional operations may be included, as will be appreciated by those of skill in the art. For example, some embodiments may include only aspects of operation 206, signal processing, while the remaining operations are performed separately. Some embodiments may not make use of an auxiliary noise detection device and therefore may not employ operation 205. In some embodiments, a computer (F) may be involved in some or all of the illustrated operations, for example by initiating and/or controlling the illustrated operations, however it will be appreciated that the computer (F) need not be involved in all of the illustrated operations, and some aspects of operations may be performed by human or electronic agents outside of the computer (F). For example, certain operations may be initiated or otherwise controlled using electronics separate from and outside of the computer (F).

Generating a Static Magnetic Field

Components and methods configured to generate a static magnetic field B0 within a sample of interest may include a static magnetic field generating device (A) equipped with one or more magnets. In the application of noise canceling in-situ NMR to detecting and characterizing fluids within an Earth formation, a static magnetic field generating device (A) may include one or more permanent magnets configured for deployment within a borehole. One or more permanent magnets and may be arranged to create a static magnetic field of a predetermined value selected for the desired application, within an NMR sensitive region (D) inside the sample of investigation. A computer (F) may be used to control a borehole suspension system to control the depth (location) of the static magnetic field generating device (A) in the borehole, or the suspension system may be controlled manually or via separate electronics.

In some embodiments, static magnetic field generating device (A) may include magnets located at any location from which a magnetic field can be created in the NMR sensitive region (D). The static magnetic field generating device (A) need not be located inside a loop of the alternating magnetic field generator (B) as illustrated in the appended figures. Also, static magnetic field generating device (A) may comprise any device configured to produce a static magnetic field, including, for example, electromagnets as well as permanent magnets. In some embodiments, an in-situ NMR apparatus may be configured for operation without static magnetic field generating device (A): an in-situ NMR apparatus may instead be configured to rely on an environmentally innate magnetic field, such as the earth's magnetic field.

Generating an Alternating Magnetic Field and Detecting NMR

Components and methods configured to generate an alternating magnetic field B1 to actuate an NMR process within the sample of interest may include an alternating magnetic field generator (B) comprising one or more antennas or coil arrays. In borehole applications, the one or more antennas or coil arrays may be configured for deployment within a borehole. The computer (F) may control a transmit switch and power amplifier. The alternating magnetic field generator (B) can be activated by closing the transmit switch and activating the power amplifier to direct alternating current to the alternating magnetic field generator (B).

It will be understood with the benefit of this disclosure that in the various embodiments, the alternating magnetic field generator (B) and the NMR detection device (C) may be implemented using a same antenna, induction coil, or array, e.g., as illustrated in FIG. 1, or they may be implemented through separate antennas, coil(s), and/or arrays. In FIG. 1, the alternating magnetic field generator (B) and the NMR detection device (C) are implemented in a figure-eight comprising two coils, a top coil and a bottom coil, as shown. Either or both of the coils in the figure-eight may be used as magnetic field generator (B), and either or both of the coils in the figure-eight may also be used as the NMR detection device (C).

Attenuating Noise and Measuring NMR

Turning now to components and methods configured to attenuate electromagnetic noise and measure NMR, the term "noise" as used herein refers to any and all EM noise and/or EM interference, including but not limited to RF noise as well as any other form of Electromagnetic Interference (EMI).

Existing devices and methods for performing in-situ NMR measurements are generally well suited to their intended purposes, but they are not configured for noise cancellation and as a result, not well suited to performing in-situ NMR measurements in the presence of noise. The present disclosure recognizes that a significant problem with conventional NMR systems is that devices designed for in-situ NMR detection may not be practical for some applications because they do not adequately reduce electromagnetic noise or interference that can degrade or obscure the desired NMR signals.

For example, in-situ NMR devices designed for deployment in deep boreholes, deeper than 100 meters, where electromagnetic noise and interference is often effectively shielded by the large amount of electrically conducting Earth between Earth's surface and the in-situ NMR sensor, may be less effective in near-surface applications at depths of 100 meters or less. Deep boreholes are common in oil and gas exploration, while groundwater exploration is often conducted closer to the earth's surface.

In near-surface applications the amount of electrical shielding provided by the Earth is generally much lower, and significant levels of electromagnetic noise can propagate through the shallow Earth to the in-situ NMR sensor. NMR sensor designs with insufficient means of canceling such noise are less effective in noisy environments. The problem of noise is compounded by electrically conducting cables used to physically support and communicate with the borehole NMR device, which can act as conduits for noise, and can enable above ground noise sources to affect the NMR measurement in the borehole. Furthermore, electronic components and power generation devices within the borehole can create noise in the vicinity of the borehole NMR detection device, and these instrumentation noise sources can interfere with the detection of NMR signals.

Referring again to the generic noise canceling in-situ NMR detection apparatus depicted in FIG. 1, in some embodiments this new apparatus may comprise one or more components configured to attenuate electromagnetic noise. Example components configured to attenuate noise include an NMR detection device (C) configured to cancel noise, and an auxiliary noise detection device (E). Both of these example components are described in detail herein.

In some embodiments, an NMR detection device (C) may be configured to attenuate noise through the use of a noise canceling design. For example, an NMR detection device (C) may be configured as a series combination of two or more induction coils of equal or substantially equal effective area, the coils separated by some distance d and with their winding phases in opposite directions. The distance d between the coils may be, e.g., a distance between centers of the coils. FIG. 1 illustrates two coils wherein the centers of the coils are clearly separated by a distance. The term "substantially equal" is used herein to account for the fact that there may be some margin of error, depending on the design requirements of a particular system. Substantially equal implies as much equality as is practical given the various design requirements of a particular system.

In some embodiments, components and methods configured to detect the actuated NMR process within the sample of interest, and components and methods configured to attenuate noise may be implemented via a NMR detection device (C) configured as noise canceling antenna. A noise canceling antenna may be sensitive to the localized NMR process of interest and may be simultaneously insensitive to spatially homogeneous noise fields.

In some embodiments, a noise canceling antenna may be configured with non-zero spatial sensitivity to the NMR signals generated by a sample, e.g., NMR signals generated by an earth formation under investigation, and the noise canceling antenna may also be configured to provide reduced or zero spatial sensitivity to noise.

An example noise canceling antenna configuration, shown in FIG. 1, may comprise two or more laterally or vertically displaced NMR detection coils of equal effective area but with opposite polarity. The NMR detection coils may be wired in series to each other such that the combined series coil is insensitive to spatially homogenous magnetic fields. In some embodiments, the coils may be formed from a single wire (or multiple wires in series), with both ends of the wire coupled to electronics comprising computer (F), while the length of the wire is configured to adjustably position the noise canceling antenna within an in-situ sample to be measured. The length of wire may be configured as a noise canceling antenna by forming the wire in a first loop, then crossing the wire and forming an additional loop, as shown in FIG. 1. To separate the loops by any desired distance, the wire may for example form the first loop, then may be twisted to form a length of twisted wire for a desired separation distance, and then may be formed in the additional loop. In some embodiments, the NMR detection coils may be wired in series to each other using a passive or active switching circuit such that the combined series coil is insensitive to spatially homogenous magnetic fields when the switching circuit is effectively closed. The NMR detection coils may be arranged in a figure-eight, as illustrated in FIG. 1.

An NMR detection coil (C) may be configured to detect a desired NMR signal process primarily in loop(s) of the coil closest to the NMR sensitive region (D), while loop(s) of the coil further from the NMR sensitive region (D) serve to cancel noise. For example, in FIG. 1, the upper loop of the figure-eight implementing the NMR detection device (C) may have reduced sensitivity to the NMR sensitive region (D), compared to the lower loop of the figure-eight, due to the added distance between the upper loop and the NMR sensitive region (D). Both loops of the NMR detection coil (C) may measure the incident noise field (G). However, because the windings of the coils are of opposite phase, the induced voltages from the noise field (G) on each coil may be of opposite polarity and hence the noise voltage at the terminals of the combined detection coil may be significantly reduced.

In some embodiments, as illustrated in FIG. 1, an in-situ NMR detection device (C) may be configured for placement in a borehole. Configuring a component for placement in a borehole may comprise forming the component to a width and length that are designed to fit within the borehole. Also, a component may be provided with structural support, suspension couplings and so forth to allow for placement and orientation in a borehole environment.

It will be further understood that the various embodiments disclosed herein need not be restricted to the use of a single NMR detection device (C), but are applicable to in-situ NMR apparatus employing a plurality of NMR detection devices.

Auxiliary Noise Detection

Additional example components and methods configured to attenuate noise may include an auxiliary noise detection device (E). An example auxiliary noise detection device is an auxiliary antenna or coil, which may be implemented in addition to a NMR detection device (C), so that the noise canceling in-situ NMR apparatus is a multi device/multicoil apparatus comprising one or more NMR detection devices (C), and one or more auxiliary noise detection devices (E).

The one or more auxiliary noise detection devices (E) may be located in-situ and/or external to the sample under investigation, and may be configured to detect noise. A computer (F) and/or digital signal processor may be configured to combine sampled data from the NMR detection device (C) and the one or more auxiliary noise detection devices (E), so as to enhance a desired NMR signal and reduce unwanted noise in the output.

In some embodiments, one or more auxiliary noise detection devices may be designed and positioned to be sensitive to noise sources and insensitive to the NMR process within a sample under investigation. Separate detection electronics and recording channels may be used for the NMR detection device (C) and the one or more auxiliary noise detection devices (E). Noise data collected at a noise detection device (E) may be reduced or eliminated from NMR detection channel data gathered at (C), for example through digital signal processing performed in the computer (F), optionally using correlation cancellation as the mathematical approach and criterion for optimizing the cancellation of noise.

In some embodiments, the one or more auxiliary noise detection devices (E) may be configured to detect an incident noise field (G). An NMR spectrometer within computer (F) may be configured to sample and record signals from both the NMR detection device (C), and the one or more auxiliary noise detection devices (E), on separate data channels.

The computer (F) may be configured to cancel a noise process on the NMR detection channel in software, using a multi-channel processing algorithm. It will be understood that the software or algorithm used to cancel the noise in post-processing is not limited to any particular mathematical technique, algorithm or optimization criterion, but that the noise cancellation algorithm includes any and all mathematical algorithms and software methods that use data from an auxiliary noise detection device (E) to cancel or reduce noise levels measured on the NMR detection device (C).

Referring again to FIG. 1 it will be understood that the use of auxiliary detection devices is not limited to the use of a single auxiliary detection device (E) as shown in FIG. 1, but may be extended to the use of a plurality of auxiliary detection devices. It is further understood that the design of said auxiliary detection devices need not be limited to a simple induction coil as shown in FIG. 1, but includes any detection device that is useful for measuring any electromagnetic noise field(s) that could interfere with detection of the NMR sample under investigation. Potentially useful detection devices for auxiliary detection devices include, but are not limited to: single-turn or multi-turn induction coils, magnetic field detection devices including magnetometers and superconducting quantum interference devices (SQUIDs), electric field detection devices including electric field sensors and antennas, and magneto-acoustic detection devices. It will be further understood that the placement, orientation and distribution of auxiliary detection devices need not be constrained to the geometry depicted in FIG. 1, and that the placement, orientation and distribution of auxiliary detection devices may be chosen arbitrarily so as to measure the electromagnetic noise field(s) as needed in any particular application. It will be understood that this includes the placement of auxiliary sensors at any location including within a sample under investigation or outside a sample under investigation, within an Earth formation borehole or outside of an Earth formation borehole, and as close to or as far away from the NMR sensitive region as necessary.

In some embodiments, an NMR detection device (C), e.g. a primary NMR detection antenna or coil, may be located in a borehole in the vicinity of the Earth formation under investigation, and one or more auxiliary noise detection devices (E) may be located on or above the surface of the Earth to detect noise. An auxiliary noise detection device (E) may comprise an induction coil configured for placement on or near the surface of the earth, for example by having appropriate length and weather protection. In some embodiments, one or more auxiliary noise detection devices may be located within the borehole or near the sample of interest, and these auxiliary noise detection devices may be designed to have a reduced spatial sensitivity to the NMR process in the sample of interest compared to the NMR detection device (C).

It will be understood that the various components and methods configured to attenuate noise described herein, namely the use of a NMR detection device (C) with reduced sensitivity to noise, and the use of auxiliary noise detection device(s) (E) to measure the noise separately and cancel it in post processing software executed by computer (F), may be implemented separately or in conjunction with each other. That is, the disclosed components and corresponding methods may be implemented together as depicted in FIG. 1, or separately as depicted in various subsequent figures.

Further Embodiments

Figure 3:
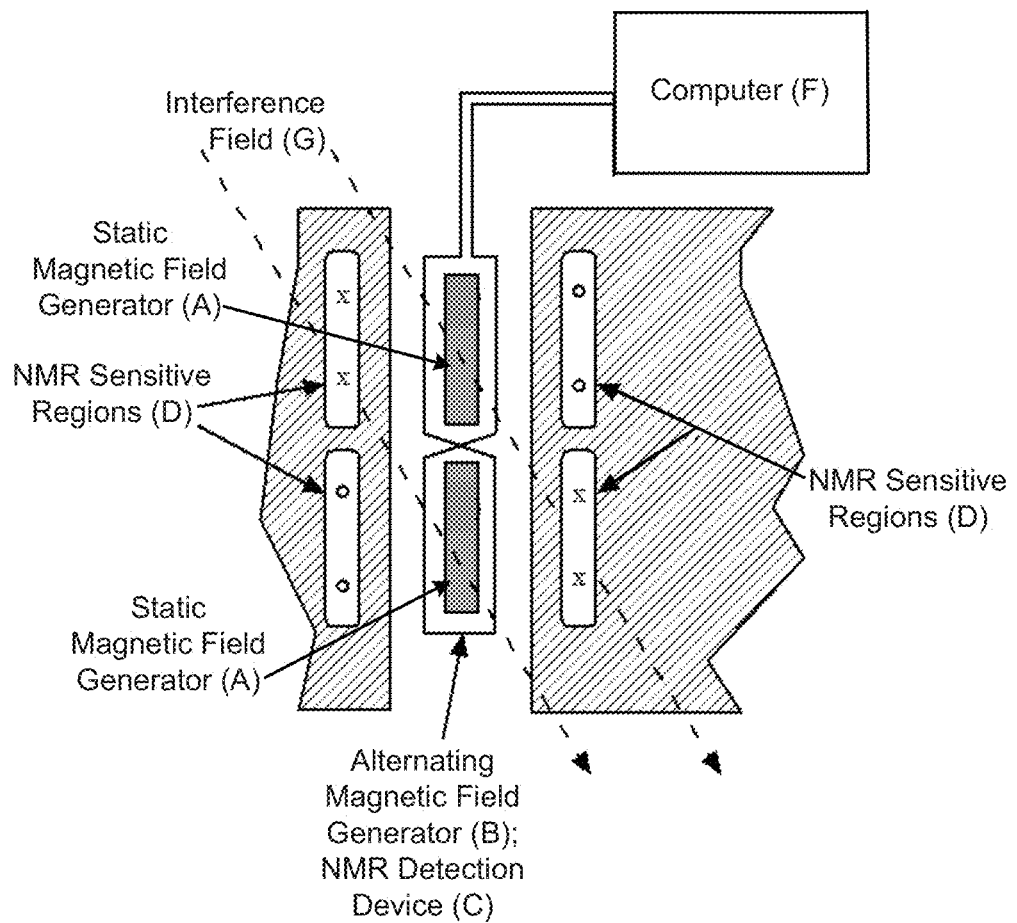
FIG. 3 is a diagram illustrating example components of noise canceling in-situ NMR detection apparatus in accordance with some embodiments of the present disclosure.

We now turn to further embodiments, as illustrated in FIGS. 3-6. FIG. 3 depicts an embodiment configured to utilize two multiple static magnetic field generating devices (A) and a figure-eight shaped coil (B,C) configured to generate an alternating excitation field and to detect the NMR signals from the NMR sensitive regions (D) within the sample. The size, shape, and location of the sensitive regions (D) may be determined in part by the operating frequency and operating bandwidth. For example, the static magnetic field intensity and the NMR resonant frequency generally decreases as the distance from the static field source(s) increases. In some embodiments, the coil (C) may comprise two or more spatially displaced sensing coils wired in series with opposite polarity such that the combined coil is sensitive to an NMR process localized within an Earth formation, and also has reduced sensitivity to spatially homogeneous noise fields The static magnetic field generating devices (A) may be designed and oriented to project static magnetic fields in a substantially similar direction. If the static magnetic field generating devices (A) are permanent magnets, then the positive poles of the magnets may face in a substantially similar direction. The localized directional fields of the figure-eight shaped coil operating as a component configured to generate an alternating magnetic field B1 (B) may be operated in transmit mode, causing NMR precession within the NMR sensitive zones (D) of the sample to have alternating phases depicted as "x" and "o" depending on the proximity of each NMR sensitive zone to each half of the figure-eight shaped coil.

In receive mode, the directional fields of the figure-eight shaped coil operating as a NMR detection device (C) may be coincident to the alternating excitation fields that determine the phase of the NMR precession at every point in the NMR sensitive region (D). Hence the induced voltages on the NMR detection device (C) due to the precessing spins throughout the NMR sensitive regions (D) of the sample may add coherently and form a non-zero combined NMR voltage signal at the detection coil terminals of the NMR detection device (C).

An incident spatially homogeneous noise field, however, may induce noise voltages of equal amplitude but opposite polarity on the individual loops of the figure-eight shaped detection coil. Hence, on the terminals of the series combined figure-eight coil, the induced noise voltage is zero for a perfect figure-eight geometry and for a perfectly spatially homogeneous noise field. For imperfect figure-eight geometries and inhomogeneous noise fields as may be encountered in the real world, the combined noise voltage may be nonzero but may nonetheless be attenuated and therefore improve the NMR measurement.

It will be understood that the embodiment depicted in FIG. 3 can be realized using an NMR detection device (C) comprising a pair of displaced single or multi-turn loops of equal effective area, or by any other pair of magnetic field generating and detecting devices that, when connected in series, cause significant attenuation of electromagnetic noise at the combined detection device terminals compared to the electromagnetic noise sensed by either of the individual magnetic field detecting devices independently.

Figure 4:
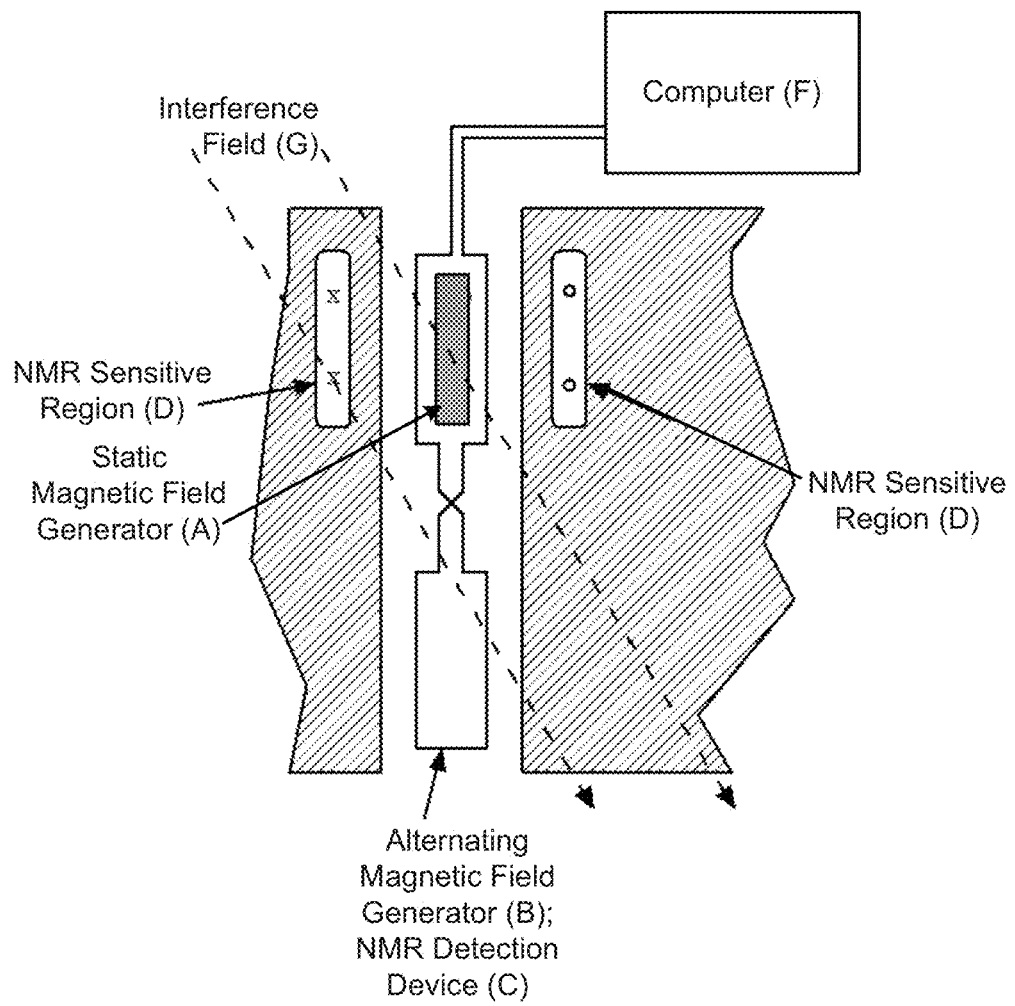
FIG. 4 is a diagram illustrating example components of noise canceling in-situ NMR detection apparatus in accordance with some embodiments of the present disclosure.

FIG. 4 depicts another embodiment, which may utilize a single static magnetic field generating device (A) and a figure-eight shaped alternating magnetic field generating device and NMR detection device (B,C). This embodiment may operate in similar fashion to the embodiment depicted in FIG. 3, except that the NMR sensitive zone (D) may be concentrated in the vicinity of only one of the two loops that constitute the figure-eight. As such, the lower loop of the figure-eight (in this example) may have reduced sensitivity to the NMR sensitive zone (D) and the majority of NMR signal may be detected via the upper loop. The upper and lower loops may be wound in opposite sense (opposite polarity) and may have a same effective area such that a spatially homogeneous noise field (G) may be attenuated or canceled at the coil terminals of the combined figure-eight coil.

It will be understood that the distance between the two loops in the figure-eight, the number of loops, and the orientation of the loops need not be restricted to the scale shown in FIG. 3 or 4, and the distance between the loops may be relatively large or small depending on the requirements of the application, and the number of loops, orientation of the loops and size of the loops may also vary. It will be also understood that the embodiment depicted in FIG. 4 can be realized using a NMR detection coil (C) comprising a pair of displaced single or multi-turn loops of substantially equal effective area, or by any other pair of magnetic field generating and detecting devices that, when connected in series, cause attenuation of electromagnetic noise at the combined detection device terminals compared to the electromagnetic noise sensed by either of the individual magnetic field detecting devices independently.

Figure 5:
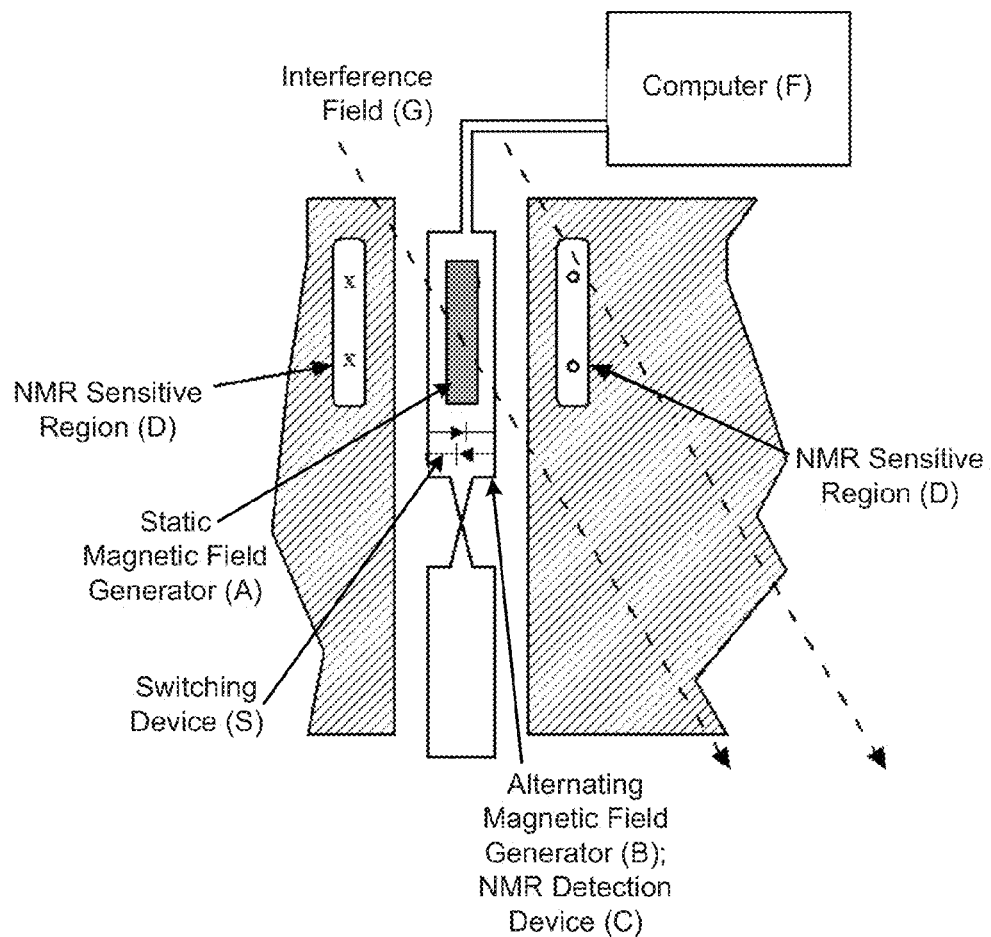
FIG. 5 is a diagram illustrating example components of noise canceling in-situ NMR detection apparatus in accordance with some embodiments of the present disclosure.

FIG. 5 depicts another embodiment, which utilizes a single static magnetic field generating device (A) and a figure-eight shaped alternating magnetic field generating device and NMR detection device (B,C) wherein the loops of the figure-eight may be connected in series with an active or passive switching device (S) providing a short circuit bypass of one or more of the loops (e.g., the lower loop) during the transmit excitation pulse. An active switching device may include actively controlled electronic circuits that create open or closed circuits. A passive switching device may include diodes, including crossed diode pairs, or other semiconductors that cause a circuit to switch from the open to closed circuit states depending on the level of a voltage applied to the passive switching device(s). This embodiment may operate in a fashion similar to the embodiment shown in FIG. 4, except that during the transmit excitation pulse some or all of the excitation pulse current may be shunted away from the bypassed loop(s). This provides the advantages of reducing the overall coil impedance during transmit excitation pulse and also reducing the possibility of generating NMR signals in the vicinity of the bypassed loop(s), which may improve the spatial resolution of the noise canceling in-situ NMR measurement device.

In some embodiments an NMR apparatus according to FIG. 5 may be configured with a static magnetic field generating device and a detection device that may for example comprise two or more spatially displaced sensing coils wired in series with opposite polarity and using a passive switch comprising parallel crossed diodes such that the combined coil is sensitive to the NMR process localized within the Earth formation and also has reduced sensitivity to spatially homogeneous noise fields and such that during transmit mode the transmit current may be routed primarily within the coil that is adjacent to the NMR sensitive region.

Figure 6:
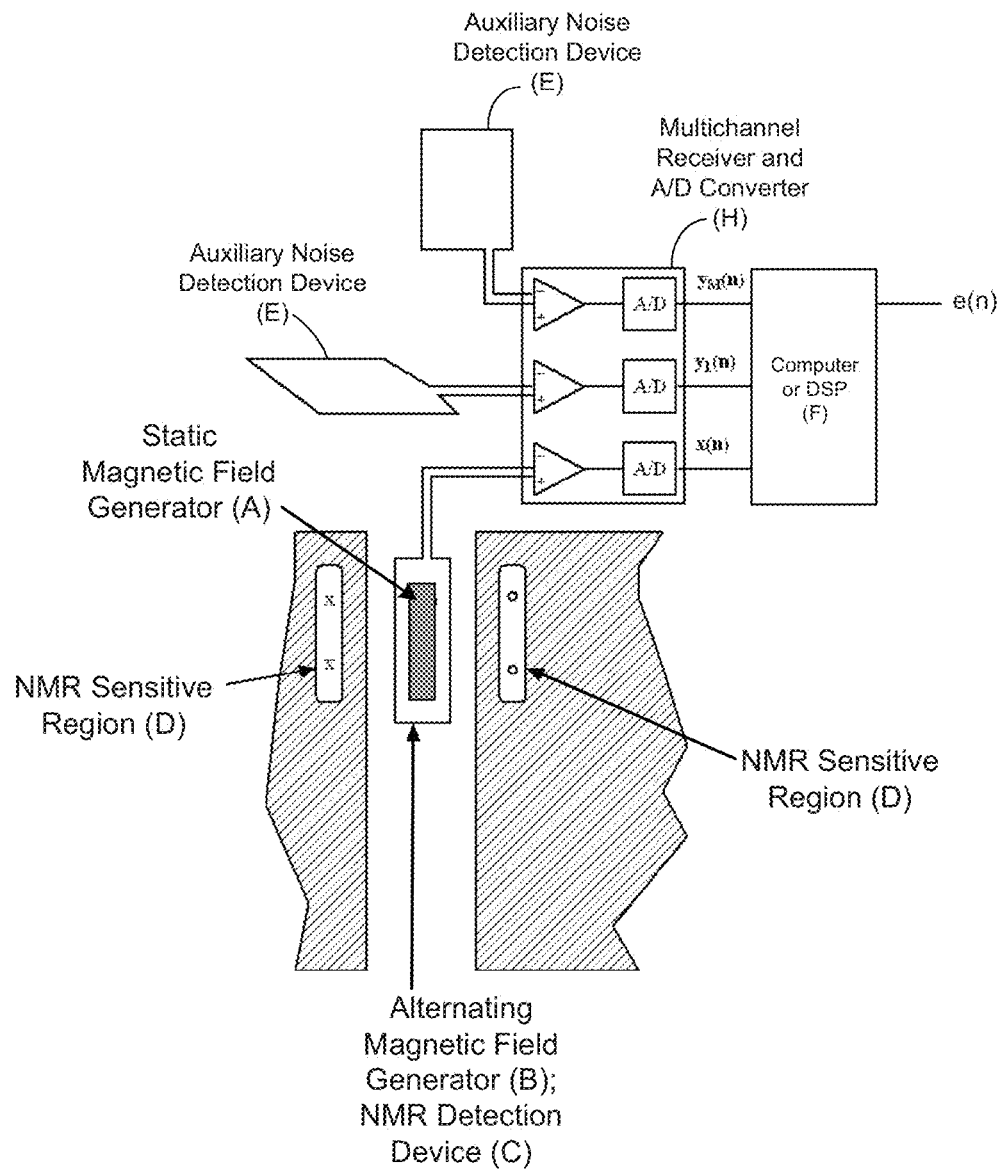
FIG. 6 is a diagram illustrating example components of noise canceling in-situ NMR detection apparatus in accordance with some embodiments of the present disclosure.

FIG. 6 depicts an embodiment that may use a single static magnetic field generating device (A), an alternating magnetic field generating device and NMR detection device (B,C) that may be sensitive to the NMR process produced in an NMR sensitive region (D) localized within an Earth formation, auxiliary noise detection devices (E) to detect noise and interference noise sources, a multichannel receiver and analog to digital converter (H) configured to sample data from the NMR detection device (C) and auxiliary noise detection devices (E), and a computer (F) configured with software to combine the sampled data x(n) from the NMR detection device (C), and the sampled data $y_1(n) \ldots y_M(n)$ from the auxiliary detection devices (E), to produce a sampled output sequence e(n) that may contain the desired NMR signal process but with attenuated noise or interference compared to the sampled data x(n). A multichannel receiver and analog to digital converter (H) may comprise signal amplifiers and Analog to Digital (A/D) converters for one or more channels, as shown. A multichannel receiver and analog to digital converter (H) may comprise a separate component from the computer (F) or may be integrated with the computer (F) in some embodiments.

FIG. 6 illustrates an embodiment of an alternating magnetic field generating device and NMR detection device (B,C) that comprises a single induction coil. It should be understood that the alternating magnetic field generating device (B) may be configured as a single induction coil in some embodiments, whether or not the alternating magnetic field generating device (B) is combined with the NMR detection device (C). Similarly, the NMR detection device (C) may be configured as a single induction coil in some embodiments, whether or not NMR detection device (C) is combined with the alternating magnetic field generating device (B). Also, the NMR detection device (C) in FIG. 6 is an example of a NMR detection device (C) that does not include a noise-canceling design. An NMR detection device (C) that does not include a noise-canceling design may include a single induction coil as shown, an array of coils, or any other device described herein as capable of detecting NMR. The NMR detection apparatus of FIG. 6 is nonetheless noise-canceling because noise may be detected at the auxiliary detection devices (E) and canceled from the NMR measurements collected via the NMR detection device (C).

In FIG. 6, it will be understood that this embodiment need not be restricted to the use of two auxiliary noise detection devices (E), as depicted in FIG. 6, but the embodiment may incorporate any number of auxiliary noise detection devices, and these auxiliary noise detection devices may take any form encompassing all classes of devices capable of detecting electromagnetic fields, including but not limited to: induction coils, electric and magnetic field sensors, electric field antennas, magnetometers, and superconducting quantum interference devices. It is further understood that the auxiliary noise detection devices may be located and oriented in any arrangement that suits a given application, including placement of auxiliary noise detection devices within a borehole or on or above the surface of the Earth, and within or external to a sample under investigation. It will be further understood that this embodiment does not require any particular software or mathematical algorithm used to process the multi-sensor data so as to cancel or attenuate noise in the output sequence e(n). The apparatus and procedure for simultaneously acquiring data on a NMR detection device and one or more auxiliary noise detection devices may provide independent measurements of the noise field(s), this independent noise data may enable cancellation of the noise processed(s) recorded on the NMR detection device data channel. It will be understood by those skilled in the art of signal processing with the benefit of this disclosure that many different mathematical algorithms and software methods may be suitable for effectively canceling noise on a NMR detection device channel using noise data detected on separate auxiliary noise detection devices and recorded on separate noise data channels.

Processing

Figure 7:
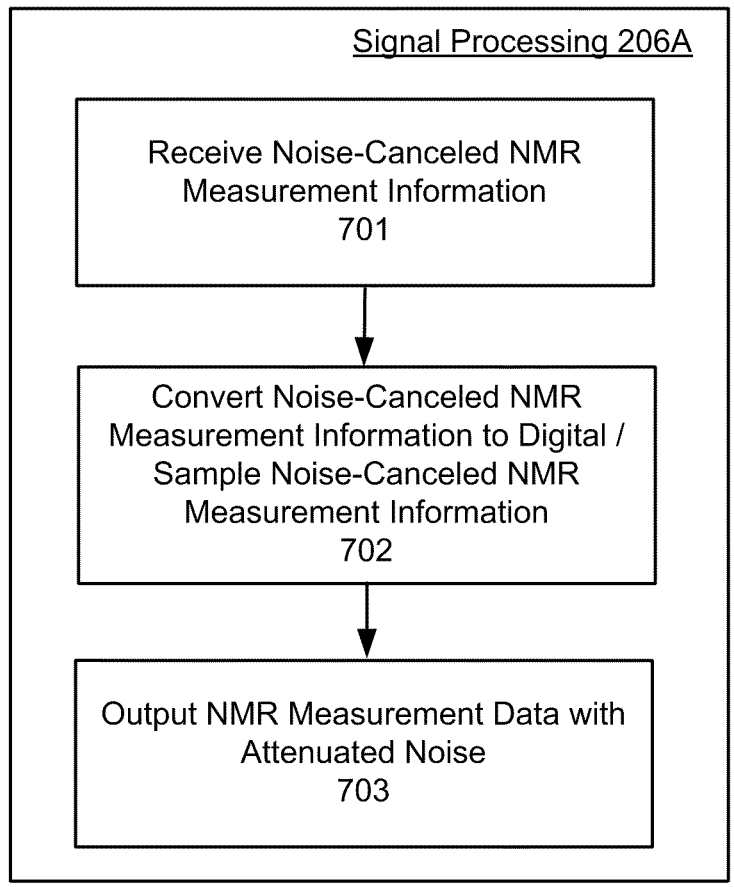
FIG. 7 is a diagram illustrating an example signal processing method.

FIG. 7 is a diagram illustrating an example signal processing method. In some embodiments, a computer (F) may be configured to perform signal processing operations 206A. Signal processing operations 206A may comprise a "Receive Noise Canceled NMR Measurement Information" operation 701, a "Convert Noise Canceled NMR Measurement Information to Digital/Sample Noise Canceled NMR Measurement Information" operation 702, and/or a "Output NMR Measurement Information with Attenuated Noise" operation 703.

The term "measurement information" as used herein refers to measurement information in any form. For example, measurement information may be in the form of an analog signal or in the form of digital data. In some embodiments, measurement information may be initially available in analog form, and may be converted to digital for example by sampling the analog signal.

In a "Receive Noise Canceled NMR Measurement Information" operation 701, a noise canceled signal may be received, for example from a noise canceling in-situ NMR detection device such as (C), wherein the NMR detection device comprises a built-in noise canceling architecture, so that the noise components of signals produced by the NMR detection device are at least partially attenuated. In some embodiments, a noise canceled NMR measurement information may be received indirectly. For example, data collection and processing may be performed by separate devices in some embodiments. NMR measurement information may be received from a device that initially collected signal data (e.g. directly from a NMR detection device (C)), or from some intermediate device or computer readable medium.

In a "Convert Noise Canceled NMR Measurement Information to Digital/Sample Noise Canceled NMR Measurement Information" operation 702, received noise-canceled signals which may comprise analog signals may be converted to digital, for example by sampling the analog signal. Any desired sampling rate may be used. Digital signals and data may also be demodulated, "down-sampled" or "up-sampled" in some embodiments.

In a "Output NMR Measurement Information with Attenuated Noise" operation 703 Noise Canceled NMR Samples resulting from operation 702 and any further operations such as, for example, a filtering operation, may be recorded on a computer readable medium and/or graphically displayed via a display device.

Figure 8:
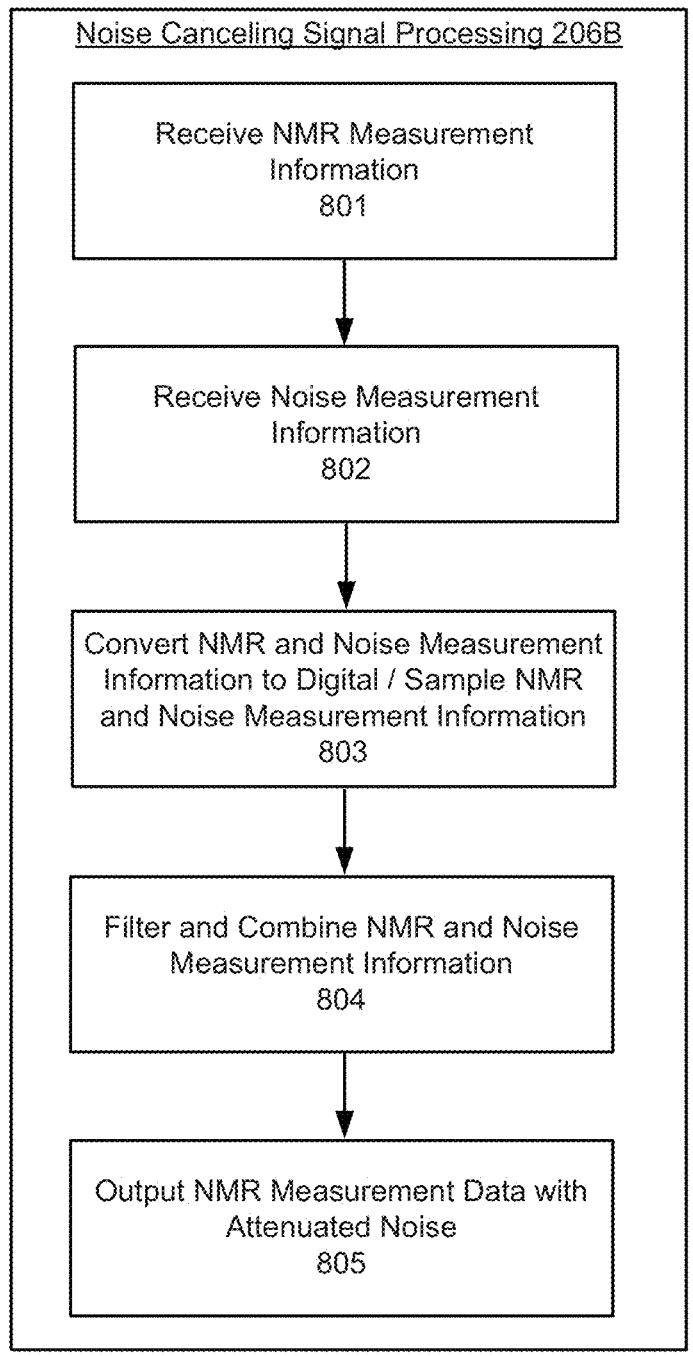
FIG. 8 is a diagram illustrating an example signal processing method.

FIG. 8 is a diagram illustrating an example signal processing method. In embodiments configured to receive one or more signals from auxiliary noise detection device(s) (E), the computer (F) may be configured to perform noise canceling signal processing operations 206B. Noise canceling signal processing operations 206B may comprise a "Receive NMR Measurement Information" operation 801, a "Receive Noise Measurement Information" operation 802, a "Convert NMR and Noise Measurement Information to Digital/Sample NMR and Noise Measurement Information" operation 803, a "Filter and Combine NMR and Noise Measurement Information" operation 804, and/or a "Output NMR Measurement Information with Attenuated Noise" operation 805.

In a "Receive NMR Measurement Information" operation 801, NMR signals may be received from an in-situ NMR detection device such as (C). The received NMR signals may be noise-canceled as described above with reference to step 701, or may not be noise canceled. In either case, the received signals may be subject to further processing to remove of noise, based on auxiliary nose measurements.

In a "Receive Noise Measurement Information" operation 802, noise signals may be received from one or more auxiliary noise detection devices such as (E). In some embodiments, the noise signals may be received from an intermediate device or computer readable medium.

In a "Convert NMR and Noise Canceled Measurement Information to Digital/Sample NMR and Noise Canceled Measurement Information" operation 803, received NMR and noise-canceled signals which may comprise analog signals may be converted to digital, for example by sampling the analog signal. Any desired sampling rate may be used. Digital signals and data may also be demodulated, "down-sampled" or "up-sampled" in some embodiments.

In a "Filter and Combine NMR and Noise Measurement Information" operation 804, NMR and noise samples may be filtered by one or more digital filters, and combined in a manner that subtracts noise from NMR data. Further discussion of an example filtering architecture and corresponding methods are discussed below with reference to FIG. 10.

In a "Output NMR Measurement Information with Attenuated Noise" operation 805, noise canceled NMR data resulting from operation 803 and any further operations as may be performed, may be recorded on a computer readable medium and/or graphically displayed via a display device.

In some embodiments of a noise canceling digital signal processing method disclosed herein, the computer (F) may be configured to sample data from an NMR detection channel, also referred to herein as a primary channel, corresponding to the NMR detection device (C), thereby producing NMR samples. The computer (F) may be configured to sample data from one or more noise channels, also referred to as auxiliary channels, corresponding to the one or more auxiliary noise detection devices (E), thereby producing noise samples. The computer (F) may be configured to digitally filter the NMR samples and/or noise samples, thereby producing filtered samples. The computer (F) may be configured to subtract filtered noise samples from filtered NMR samples to produce noise-corrected NMR output data.

In some embodiments, the computer (F) may be configured to first control the various components described herein to measure NMR and noise, as described above in connection with operations 201-205 of FIG. 2. The computer (F) may also be configured to receive and process NMR signals from the NMR detection device (C) in a signal processing operation 206. Some embodiments may comprise a single computer for both NMR measurement control and signal processing, while other embodiments may comprise separate computers for NMR measurement control and signal processing. Therefore, embodiments of this disclosure may, but need not be configured to include both NMR measurement control and signal processing.

FIG. 9 is a diagram illustrating an example computing device as may be configured to perform aspects of this disclosure. Computing system (F) may include for example a processor 110, memory 120, system bus 130, one or more drives 140, user input interface 150, output peripheral interface 160, and network interface 170.

Drives 140 may include, for example, a compact disk drive 141 which accepts an optical disk 141A, a so-called hard drive 142, which may employ any of a diverse range of computer readable media, and a flash drive 143 which may employ for example a Universal Serial Bus (USB) type interface to access a flash memory 143A. Drives may further include network drives and virtual drives (not shown) accessed via the network interface 170.

The drives 140 and their associated computer storage media provide storage of computer readable instructions, data structures, program modules and other data for the computer system (F). For example, a hard drive 142 may include an operating system 144, application programs 145, program modules 146, and database 147. Software aspects of the technologies described herein may be implemented, in some embodiments, as computer readable instructions stored on any of the drives 140 or on network 172, which instructions may be loaded into memory 120, for example as modules 123, and executed by processor 110.

Computer system (F) may further include a wired or wireless input interface 150 through which selection devices 151 and input devices 152 may interact with the other elements of the system (F). Selection devices 151 and input devices 152 can be connected to the input interface 150 which is in turn coupled to the system bus 130, allowing devices 151 and 152 to interact with processor 110 and the other elements of the system (F). Interface and bus structures that may be utilized to implement 150 may include for example a Peripheral Component Interconnect (PCI) type interface, parallel port, game port and a wired or wireless Universal Serial Bus (USB) interface.

Selection devices 151 such as a mouse, trackball, touch screen, or touch pad allow a user to select among desired options and/or data views that may be output by the system (F), for example via the display 162. Input devices 152 can include any devices through which commands and data may be introduced to the system (F). Exemplary input devices 152 include a keyboard, an electronic digitizer, a microphone, a joystick, game pad, satellite dish, scanner, media player, mobile device, or the like.

Computer system (F) may also include an output peripheral interface 160 which allows the processor 110 and other devices coupled to bus 130 to interact with peripheral output devices such as printer 161, display 162, and speakers 163. Interface and bus structures that may be utilized to implement 160 include those structures that can be used to implement the input interface 150. It should also be understood that many devices are capable of supplying input as well as receiving output, and input interface 150 and output interface 160 may be dual purpose or support two-way communication between components connected to the bus 130 as necessary.

Computing system (F) may operate in a networked environment using logical connections to one or more computers. By way of example, FIG. 9 shows a LAN 171 connection to a network 172. A remote computer may also be connected to network 171. The remote computer may be a personal computer, a server, a router, a network PC, a peer device or other common network node, and can include many or all of the elements described above relative to computing system (F).

Networking environments are commonplace in offices, enterprise-wide area networks (WAN), local area networks (LAN), intranets and the Internet. For example, in the subject matter of the present application, computing system (F) may comprise the source machine from which data is migrated, and the remote computer may comprise the destination machine, or vice versa. Note however, that source and destination machines need not be connected through a network 172, but instead, data may be migrated via any media capable of being written by the source platform and read by the destination platform or platforms.

When used in a LAN or WLAN networking environment, computing system (F) is connected to the LAN through a network interface 170 or an adapter. When used in a WAN networking environment, computing system (F) typically includes a modem or other means for establishing communications over the WAN, such as the Internet or network 172. It will be appreciated that other means of establishing a communications link between computers may be used.

Figure 10:
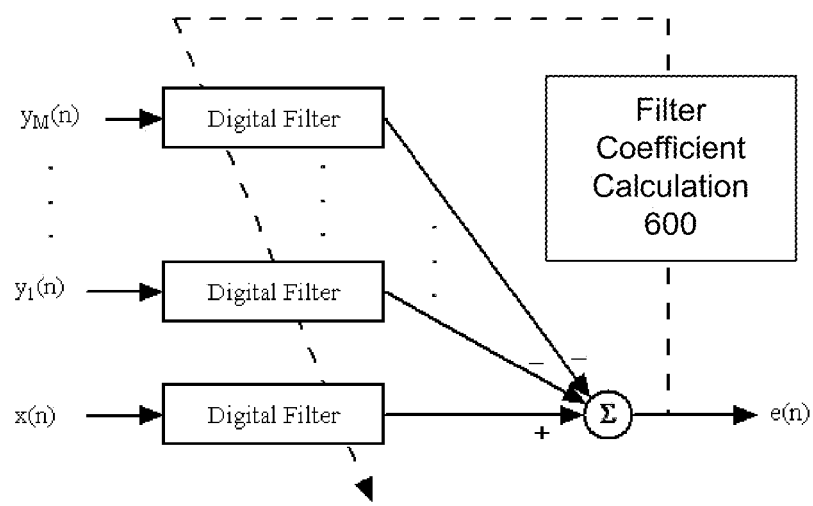
FIG. 10 is a diagram illustrating an example processing architecture and corresponding noise canceling digital signal processing methods.

According to some embodiments, computing system (F) may be configured to carry out any of the operations 201-206 illustrated in FIG. 2 and the signal processing operations 206A and 206B illustrated in FIGS. 7 and 8. Computing system (F) may be configured to comprise the multichannel receiver and analog to digital converter (H) of FIG. 6 and/or a processing architecture such as illustrated in FIG. 10. Computing system (F) may be further configured to control a variety of additional operations, such as raising and lowering components and devices such as A, B, and/or C in a borehole, conducting multiple NMR measurements and combining data from such measurements, and requesting and accepting user-entered data regarding a measurement or series of measurements such as time of measurement and location of measurement. Computer (F) may include an NMR spectrometer configured to sample and record signals from the NMR detection device (C) and/or the auxiliary noise detection device (E). Computer (F) may comprise a power amplifier configured to drive the alternating magnetic field generator (B) and/or static magnetic field generator (A). Computer (F) may comprise transmit and receive switches configured to activate the alternating magnetic field generator (B) in transmit mode, and to activate the NMR detection device (C) in receive mode. Computer (F) may comprise matching circuits and receive electronics. Computer (F) may comprise a data acquisition system configured to receive, process and record NMR measurement information and/or noise measurement information.

FIG. 10 is a diagram illustrating an example processing architecture and corresponding noise canceling digital signal processing methods. FIG. 10 depicts an embodiment of a processing architecture and corresponding noise canceling digital signal processing methods that can be configured to process data collected using the apparatus depicted in FIG. 6, so as to cancel or attenuate noise received on the NMR detection device channel. The processing architecture depicted in FIG. 10 may be implemented in the computer (F) illustrated for example in FIG. 6, further aspects of which are illustrated in FIG. 9.

The processing architecture depicted in FIG. 10 may include a digital filter for each data channel, e.g., a digital filter for an NMR detection device channel, which may be configured to receive sampled data x(n), and a digital filter for one or more auxiliary noise detection device channels, which may be configured to receive the sampled data $y_1(n) \ldots y_M(n)$. A summing operator $\Sigma$ may be configured to combine the digitally filtered data from one or more of the digital filters into a single output sequence e(n). The dashed line represents a feedback process indicating that the filter coefficients used by the digital filters for each channel may be adaptively modified, e.g., by filter coefficient calculation module 600, which may be configured to adaptively modify filter coefficients on the basis of the output sequence e(n).

It will be understood with the benefit of this disclosure that the filter coefficient calculation module 600 may be configured to use any of a variety of mathematical criterion to adapt the filter coefficients. In some embodiments, the filter coefficient calculation module 600 may be configured to adapt the filter coefficients so as to minimize the expected mean squared value of the output $E\{|e(n)|^2\}$. It will be also understood that the filter coefficient calculation module 600 may be configured to perform a variety of methods suitable for re-computing or adapting the filter weights/coefficients on the basis of the output sequence e(n). In some embodiments filter weights/coefficients may be adapted on a time-sample-by-sample basis using a Least Mean Square (LMS) algorithm or a Recursive Least Squares (RLS) algorithm. In some embodiments filter coefficients may be computed independently for separate blocks of time samples.

In some embodiments, the filter coefficient calculation module 600 may be configured to carry out aspects of noise canceling digital signal processing method using correlation cancellation as the mathematical basis for estimating the filter coefficients. Correlation cancellation may produce a set of filter coefficients that minimizes the mean squared value of the output sequence e(n). Any of a wide variety direct, block-based and iterative methods may be used to estimate the filter coefficients and minimize the mean squared value of the output e(n). Several implementations of correlation cancellation methods are known to those of skill in the art, for example as described in S. Haykin, "Adaptive Filter Theory", 1996. The various correlation cancellation methods described therein may be adapted for use with some embodiments described herein.

In some embodiments, a computer (F) may be configured to perform noise canceling digital signal processing methods that transform/digitally filter the input data for each sampled data channel via a weighted linear combination of the sampled data received on one or more of the channels.

In some embodiments, a computer (F) may be configured to channelize measurement information from one or more of the detection devices into a set of frequency channels. In some embodiments of this approach, the measurement information from one or more of the detection devices may be transformed into a set of frequency coefficients using a Discrete Fourier Transform (DFT) or other linear transform. The computer (F) may be configured to subtract the transformed noise samples/measurement information from transformed NMR samples/measurement information independently for each of a plurality of frequency channels, i.e., the correlation cancellation may be performed on separate frequency channels. The set of output signals/measurement information may be transformed back into the time domain using an inverse of the previously used DFT or other linear transform.

In some embodiments of a digital signal processing method, the computer (F) may be configured to filter and process sampled data from all of the data channels, including the primary and auxiliary channels, in one step using, for example, Space-Time Adaptive Processing (STAP). The computer (F) may be configured to use correlation cancellation as the mathematical approach for optimizing the Signal to Noise Ratio (SNR) in the processor output.

There is little distinction left between hardware and software implementations of aspects of systems; the use of hardware or software is generally (but not always) a design choice representing cost vs. efficiency tradeoffs. There are various vehicles by which processes and/or systems and/or other technologies described herein can be effected (e.g., hardware, software, and/or firmware), and that the preferred vehicle may vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation;

or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various embodiments have been disclosed herein, other aspects and embodiments will be apparent to those skilled in art.

The invention claimed is:

1. A noise canceling in-situ Nuclear Magnetic Resonance (NMR) detection device configured for deployment inside or adjacent to an earth formation, comprising:
   two or more in-situ NMR induction coils configured for deployment inside or adjacent to an earth formation, wherein at least one of the in-situ NMR induction coils serves as an alternating magnetic field generator for an NMR detection apparatus, and wherein at least one of the in-situ NMR induction coils serves as an NMR detection device for the NMR detection apparatus;
   wherein at least two of the in-situ NMR induction coils are wired in series to each other in order to form a combined series coil configured for deployment inside or adjacent to the earth formation and wherein the combined series coil includes the NMR detection device;
   wherein the at least two in-situ NMR induction coils of the combined series coil are separated by a distance d and are characterized by winding phases in opposite directions; and
   wherein the combined series coil is sensitive to NMR signals originating from within the earth formation and insensitive to spatially homogenous magnetic fields; and
   a static magnetic field generator device configured for deployment inside or adjacent to the earth formation with the combined series coil;
   wherein the static magnetic field generator device is configured to generate a static magnetic field in an NMR sensitive region inside the earth formation;
   wherein the alternating magnetic field generator is configured to generate, under control of an NMR detection apparatus, an alternating magnetic field in the NMR sensitive region inside the earth formation; and
   wherein the combined series coil is configured to detect NMR signals from the NMR sensitive region inside the earth formation, while remaining substantially insensitive to spatially homogenous magnetic fields.

2. The noise canceling in-situ NMR detection device of claim 1, wherein the combined series coil is configured as a figure-eight.

3. The noise canceling in-situ NMR detection device of claim 1, wherein the static magnetic field generator device comprises one or more permanent magnets, one or more electromagnets, or a combination of permanent magnets and electromagnets.

4. The noise canceling in-situ NMR detection device of claim 1, wherein the combined series coil comprises the induction coil serving as the alternating magnetic field generator, and
   wherein the coils of the combined series coil are wired in series to each other using a switching circuit configured to provide a short circuit bypass of one or more coils in the combined series coil, other than the alternating magnetic field generator, during operation of the alternating magnetic field generator in transmit mode, whereby the combined series coil is switchable between the transmit mode which bypasses coils other than the alternating magnetic field generator and a detection mode in which the combined series coil is sensitive to NMR signals and substantially insensitive to spatially homogenous magnetic fields.

5. The noise canceling in-situ NMR detection device of claim 1, wherein the noise canceling in-situ NMR detection device is configured for placement in an earth formation borehole.

6. The noise canceling in-situ NMR detection device of claim 1, wherein said NMR detection device is coupled to the NMR detection apparatus, the NMR detection apparatus comprising a computer configured to control NMR measurements using the noise canceling in-situ NMR detection device.

7. A noise canceling in-situ Nuclear Magnetic Resonance (NMR) detection apparatus, comprising:
   a primary in-situ NMR detection device configured for deployment inside or adjacent to an earth formation, the primary in-situ NMR detection device comprising:
   a static magnetic field generator device;
   an alternating magnetic field generator device; and
   a magnetic field detection device; comprising a combined series coil, the combined series coil including at least two NMR induction coils wired in series to each other, separated by a distance d, and characterized by winding phases in opposite directions whereby the combined series coil is sensitive to NMR signals originating from within the earth formation and the combined series coil is also insensitive to spatially homogenous magnetic fields;
   wherein the static magnetic field generator device generates a static magnetic field in an NMR sensitive region inside the earth formation, and the alternating magnetic field generator device generates an alternating magnetic field within the same NMR sensitive region inside the earth formation, and the magnetic field detection device is sensitive to NMR induced magnetic fields generated within the same NMR sensitive region inside the earth formation;
   one or more auxiliary noise detection devices;
   a multichannel receiver and one or more analog to digital converters separately coupled to the primary in-situ NMR detection device and each of the one or more auxiliary noise detection devices; and
   a computer coupled to the multichannel receiver and the one or more analog to digital converters;
   wherein the multichannel receiver and the one or more analog to digital converters are configured to receive and sample signals on a receiver primary channel designated for the primary in-situ NMR detection device in order to produce a digital sampled data output x(n) wherein the multichannel receiver and the one or more analog to digital converters are configured in order to receive and sample signals on said one or more receiver auxiliary channels designated for each of the one or more auxiliary noise detection devices in order to produce one or more digital sampled data outputs y(n);
   wherein the computer is configured with at least one computer primary channel designated for the digital sampled data output x(n) and one or more auxiliary channels designated for the one or more digital sampled data outputs y(n); and
   wherein the computer comprises a processor and a computer readable medium having instructions configured to cause the processor to:

digitally combine the digital sampled data output x(n) with the one or more digital sampled data outputs y(n) in order to produce a resulting output of NMR measurement data with attenuated noise.

8. The noise canceling in-situ NMR detection apparatus of claim 7, wherein the primary in-situ NMR detection device is a noise canceling in-situ NMR detection device.

9. The noise canceling in-situ NMR detection apparatus of claim 7, wherein the static magnetic field generator device comprises:
one or more permanent magnets, one or more electromagnets, or a combination of permanent magnets and electromagnets.

10. The noise canceling in-situ NMR detection apparatus of claim 7, wherein the primary in-situ NMR detection device is configured for placement in an earth formation borehole.

11. The noise canceling in-situ NMR detection apparatus of claim 7, wherein one or more of the auxiliary noise detection devices comprise an additional induction coil, other than the induction coils of the magnetic field detection device, wherein the additional coil is configured for placement on or above the surface of the earth formation.

12. The noise canceling in-situ NMR detection apparatus of claim 7, wherein the at least two induction coils of the combined series coil are configured as a figure-eight with winding phases in opposite directions whereby the combined series coil is sensitive to NMR signals and the combined series coil is also insensitive to spatially homogenous magnetic fields, wherein the static magnetic field generator device is located within a loop of the figure-eight, and wherein one or more of the induction coils of the combined series coil also serves as the alternating magnetic field generator device.

13. A computer configured to process Nuclear Magnetic Resonance (NMR) measurement data, comprising:
a primary channel configured to receive a digital sampled data output x(n) comprising in-situ NMR measurement information from a noise cancelling in-situ NMR detection device configured for deployment inside or adjacent to an earth formation, as claimed in claim 1, the noise cancelling in-situ NMR detection device comprising:
a static magnetic field generator device;
an alternating magnetic field generator device; and
an alternating magnetic field detection device comprising a combined series coil, the combined series coil including at least two induction coils wired in series to each other, separated by a distance d, and characterized by winding phases in opposite directions whereby the combined series coil is sensitive to NMR signals originating from within the earth formation and the combined series coil is also insensitive to spatially homogenous magnetic fields;
one or more auxiliary channels configured to receive one or more digital sampled data outputs y(n), the one or more digital sampled data outputs y(n) comprising noise measurement information resulting from measurements performed by one or more auxiliary noise detection devices, wherein the one or more auxiliary noise detection devices are separate from the noise cancelling in-situ NMR detection device; and
a processing architecture configured to digitally combine the digital sampled data output x(n) and the one or more digital sampled data outputs y(n) in order to produce a resulting output of in-situ NMR measurement data with attenuated noise, the processing architecture comprising:
a digital filter corresponding to the primary channel;
one or more additional digital filters corresponding to the one or more auxiliary channels;
a summing operator configured to combine digital filter outputs from the primary channel digital filter and the one or more additional digital filters in order to produce a resulting output sequence; and
a filter coefficient calculation module configured to calculate digital filter coefficients designated for use by the primary channel digital filter and the one or more additional digital filters.

14. The computer of claim 13, wherein the filter coefficient calculation module is configured to adaptively modify the digital filter coefficients on the basis of the resulting output sequence produced by the summing operator.

15. The computer of claim 14, wherein the filter coefficient calculation module is configured to adaptively modify the digital filter coefficients in order to minimize an expected mean squared value of the resulting output sequence produced by the summing operator.

16. The computer of claim 14, wherein the filter coefficient calculation module is configured to adaptively modify the digital filter coefficients, on a time-sample-by-sample basis, by using one or more of a Least Mean Square (LMS) algorithm, or a Recursive Least Squares (RLS) algorithm.

17. The computer of claim 14, wherein the filter coefficient calculation module is configured to adaptively modify the digital filter coefficients at least in part by using correlation cancelation in order to estimate the adaptive modifications to the digital filter coefficients.

18. The computer of claim 13, wherein the computer is further configured to:
transform the digital sampled data outputs x(n) and y(n) from the primary and auxiliary channels into a set of frequency coefficients using a linear transform;
subtract the one or more transformed digital sampled data outputs y(n) from the transformed digital sampled data output x(n) independently with respect to each of a plurality of frequency channels in order to produce a set of output measurement information; and
subsequently transform the set of output measurement information, into a time domain, using an inverse of the linear transform.

19. A method of performing a noise canceling in-situ Nuclear Magnetic Resonance (NMR) measurement, of an earth formation comprising:
deploying a noise canceling in-situ NMR detection device inside or adjacent to the earth formation, the in-situ NMR detection device comprising a combined series coil and a static magnetic field generator device;
wherein the combined series coil comprises at least two NMR induction coils wired in series, separated by a distance d, and characterized by winding phases in opposite directions whereby the combined series coil is sensitive to NMR signals originating from within the earth formation and the combined series coil is also insensitive to spatially homogenous magnetic fields;
wherein the static magnetic field generator device is configured to generate a static magnetic field in an NMR sensitive region inside the earth formation;
activating an alternating magnetic field generator device in order to apply an in-situ alternating magnetic field to the NMR sensitive region;
deactivating the alternating magnetic field generator device;
activating NMR signal detection by the in-situ NMR detection device;

receiving in-situ NMR measurement information from the in-situ NMR detection device; and transforming the in-situ NMR measurement information into a resulting output of in-situ NMR measurement data with attenuated noise.

20. The method of claim 19, further comprising receiving noise measurement information from one or more auxiliary noise detection devices, and combining the NMR measurement information and noise measurement information in order to produce the resulting output of in-situ NMR measurement data with attenuated noise.

21. The noise canceling in-situ NMR detection device of claim 1, wherein each of the at least two in-situ NMR induction coils in the combined series coil serve as the alternating magnetic field generator, and wherein each of the at least two in-situ NMR induction coils in the combined series coil serve as the NMR detection device.

22. The noise canceling in-situ NMR detection device of claim 21, wherein the static magnetic field generator device is positioned more proximal to one of the NMR induction coils of the combined series coil than to one or more other NMR induction coils thereof.

23. The noise canceling in-situ NMR detection device of claim 22, further comprising a second static magnetic field generator device positioned more proximal to another of the NMR induction coils of the combined series coil.

24. The noise canceling in-situ NMR detection device of claim 4, wherein the static magnetic field generator device is positioned more proximal to the NMR induction coil serving as the alternating magnetic field generator in the combined series coil than to one or more other NMR induction coils thereof.

25. The noise canceling in-situ NMR detection apparatus of claim 7, wherein the computer comprises a digital filter acting on the primary channel and one or more different digital filters acting on the one or more auxiliary channels, and a summing operator configured to combine resulting digitally filtered data from the digital filters into a single output sequence e(n).

26. The noise canceling in-situ NMR detection apparatus of claim 25, wherein the computer comprises a filter coefficient calculation module configured to use the output sequence e(n) in order to adaptively modify filter coefficients of each of the digital filters.

27. The noise canceling in-situ NMR detection apparatus of claim 7, wherein the computer is further configured to control an NMR measurement sequence comprising:

activating the static magnetic field generator device in order to generate a static magnetic field in the NMR sensitive region;

activating the alternating magnetic field generator device in order to generate an alternating magnetic field in the NMR sensitive region;

deactivating the alternating magnetic field generator device;

activating NMR signal detection by the in-situ NMR detection device;

activating noise signal detection by the one or more auxiliary noise detection devices; and performing signal processing by combining the digital sampled data output x(n) with the digital sampled data outputs y(n) in order to produce a resulting output of NMR measurement data with attenuated noise.

28. The noise canceling in-situ NMR detection apparatus of claim 27, wherein the in-situ NMR detection device is configured as a combined series coil configured for deployment in a borehole, the combined series coil comprising:

two NMR induction coils wired in series to each other, separated by a distance d, and configured as a figure-eight with winding phases in opposite directions whereby the combined series coil is sensitive to NMR signals and insensitive to spatially homogenous magnetic fields, wherein the combined series coil comprises the static magnetic field generator device and the alternating magnetic field generator device;

wherein the NMR induction coils of the combined series coil are wired in series to each other using a switching circuit configured to provide a short circuit bypass of one of the NMR induction coils during operation of the alternating magnetic field generator device in transmit mode, whereby the combined series coil is switchable between the transmit mode which bypasses coils other than the alternating magnetic field generator and a detection mode in which the combined series coil is sensitive to NMR signals and substantially insensitive to spatially homogenous magnetic field; and wherein the computer is further configured to control the switching circuit of the combined series coil during the NMR measurement sequence.

29. The noise canceling in-situ NMR detection apparatus of claim 7, wherein one or more of the auxiliary noise detection devices comprise an induction coil configured for placement within an earth formation borehole.

30. A method to receive and process Nuclear Magnetic Resonance (NMR) measurement data, comprising:

receiving, on a primary channel, a digital sampled data output x(n) comprising in-situ NMR measurement information from an in-situ NMR detection device configured for deployment inside or adjacent to an earth formation, the in-situ NMR detection device comprising:

a static magnetic field generator device;

an alternating magnetic field generator device; and an alternating magnetic field detection device comprising a combined series coil, the combined series coil including at least two induction coils wired in series to each other, separated by a distance d, and characterized by winding phases in opposite directions whereby the combined series coil is sensitive to NMR signals originating from within the earth formation and the combined series coil is also insensitive to spatially homogenous magnetic fields;

receiving, on one or more auxiliary channels, one or more digital sampled data outputs y(n) comprising noise measurement information from one or more auxiliary noise detection devices, which one or more auxiliary noise detection devices are separate from the in-situ NMR detection device; and digitally combining the digital sampled data output x(n) and the one or more digital sampled data outputs y(n) in order to produce a resulting output of in-situ NMR measurement data with attenuated noise, wherein the digital combining comprises:

digitally filtering the digital sampled data output x(n) with a digital filter corresponding to the primary channel;

digitally filtering the one or more digital sampled data outputs y(n) with one or more digital filters corresponding to the one or more auxiliary channels;

combining the resulting outputs of the digital filters with a summing operator in order to produce a resulting output sequence; and calculating digital filter coefficients with a filter coefficient calculation module.

31. The method of claim 30, further comprising adaptively modifying the filter coefficients, with the filter coefficient calculation module, on the basis of the resulting output sequence produced by the summing operator.

32. The method of claim 31, further comprising adaptively modifying the filter coefficients with the filter coefficient calculation module in order to minimize an expected mean squared value of the resulting output sequence produced by the summing operator.

33. The method of claim 31, further comprising adaptively modifying the filter coefficients with the filter coefficient calculation module on a time-sample-by-sample basis by using one or more of a Least Mean Square (LMS) algorithm, or a Recursive Least Squares (RLS) algorithm.

34. The method of claim 31, further comprising adaptively modifying the filter coefficients with the filter coefficient calculation module at least in part by using a correlation cancelation in order to estimate the filter coefficients.

35. The method of claim 30, further comprising:
- transforming the digital sampled data outputs $x(n)$ and $y(n)$ from the primary and auxiliary channels into a set of frequency coefficients using a linear transform; subtracting the one or more transformed digital sampled data outputs $y(n)$ from the transformed digital sampled data output $x(n)$ independently for each of a plurality of frequency channels in order to produce a set of resulting output measurement information; and
- transforming the set of resulting output measurement information back into the time domain using an inverse of the linear transform.

* * * * *